United States Patent [19]

Marple et al.

[11] Patent Number: 5,498,271
[45] Date of Patent: Mar. 12, 1996

[54] DIESEL PARTICLE VIRTUAL IMPACTOR SAMPLER

[75] Inventors: Virgil A. Marple, Maple Plain; Bernard A. Olson, Lauderdale; Kenneth L. Rubow, Plymouth, all of Minn.

[73] Assignee: MSP Corporation, Minneapolis, Minn.

[21] Appl. No.: 320,006

[22] Filed: Oct. 7, 1994

[51] Int. Cl.$^6$ ..................................................... B01D 45/06
[52] U.S. Cl. ................................ 55/321; 55/270; 55/324; 209/143
[58] Field of Search ................................ 95/32; 55/270, 55/462, 463, 464, 445, 320, 321, 337, 323, 324; 209/143, 145

[56] References Cited

U.S. PATENT DOCUMENTS

| | | | |
|---|---|---|---|
| 3,127,763 | 4/1964 | Lippmann | 73/28.06 |
| 3,938,366 | 2/1976 | Wertlake et al. | 55/445 X |
| 4,132,894 | 1/1979 | Yule | 250/435 |
| 4,133,202 | 1/1979 | Marple | 55/270 X |
| 4,321,822 | 3/1982 | Marple et al. | 55/270 X |
| 4,670,135 | 6/1987 | Marple et al. | 209/143 |
| 4,767,524 | 8/1988 | Yeh et al. | 209/143 |
| 4,827,779 | 5/1989 | Marple et al. | 73/863.22 |
| 4,941,899 | 7/1990 | Liu | 55/270 |
| 4,972,957 | 11/1990 | Liu et al. | 209/143 |

FOREIGN PATENT DOCUMENTS 61-93920(A)  5/1986  Japan .................... 73/863.22

OTHER PUBLICATIONS

*Society for Mining, Metallurgy, and Exploration, Inc.*, "Design and Evaluation of a Personal Diesel Aerosol Sampler for Underground Coal Mines", K. L. Rubow, V. A. Marple, Y. Tao, D. Liu, Society for Mining, Metallurgy, and Exploration, Inc., Littleton, CO, 1990, pp. 1–5.

*Society for Mining, Metallurgy, and Exploration, Inc.*, "3rd Symposium on Respirable Dust in the Mineral Industries", Robert L. Frantz and Raja V. Ramani, Society for Mining, Metallurgy, and Exploration, Inc., Littleton, CO, 1991, pp. 73–81.

*Mining Engineering*, "Development of personal diesel aerosol sampler design and performance criteria", B. K. Cantrell and K. L. Rubow, Feb. 1991, pp. 232–236.

Primary Examiner—Richard L. Chiesa
Attorney, Agent, or Firm—Westman, Champlin & Kelly

[57] ABSTRACT

A diesel particle virtual impactor sampler provides for a total flow through a virtual impactor after the flow passes through a classifier that removes particles substantially larger than the cutoff point of the virtual impactor. The virtual impactor has two outlets, one for minor flow and one for major flow. In a preferred embodiment, filters are used for separately filtering the major and minor flows and collecting the particles carried thereby so that a determination of the concentration of particles above and below the cutoff point can be obtained. Alternately, the major and minor flows and the particles can be passed through particle analyzer instruments for a direct particle measurement of each of the flows.

3 Claims, 2 Drawing Sheets

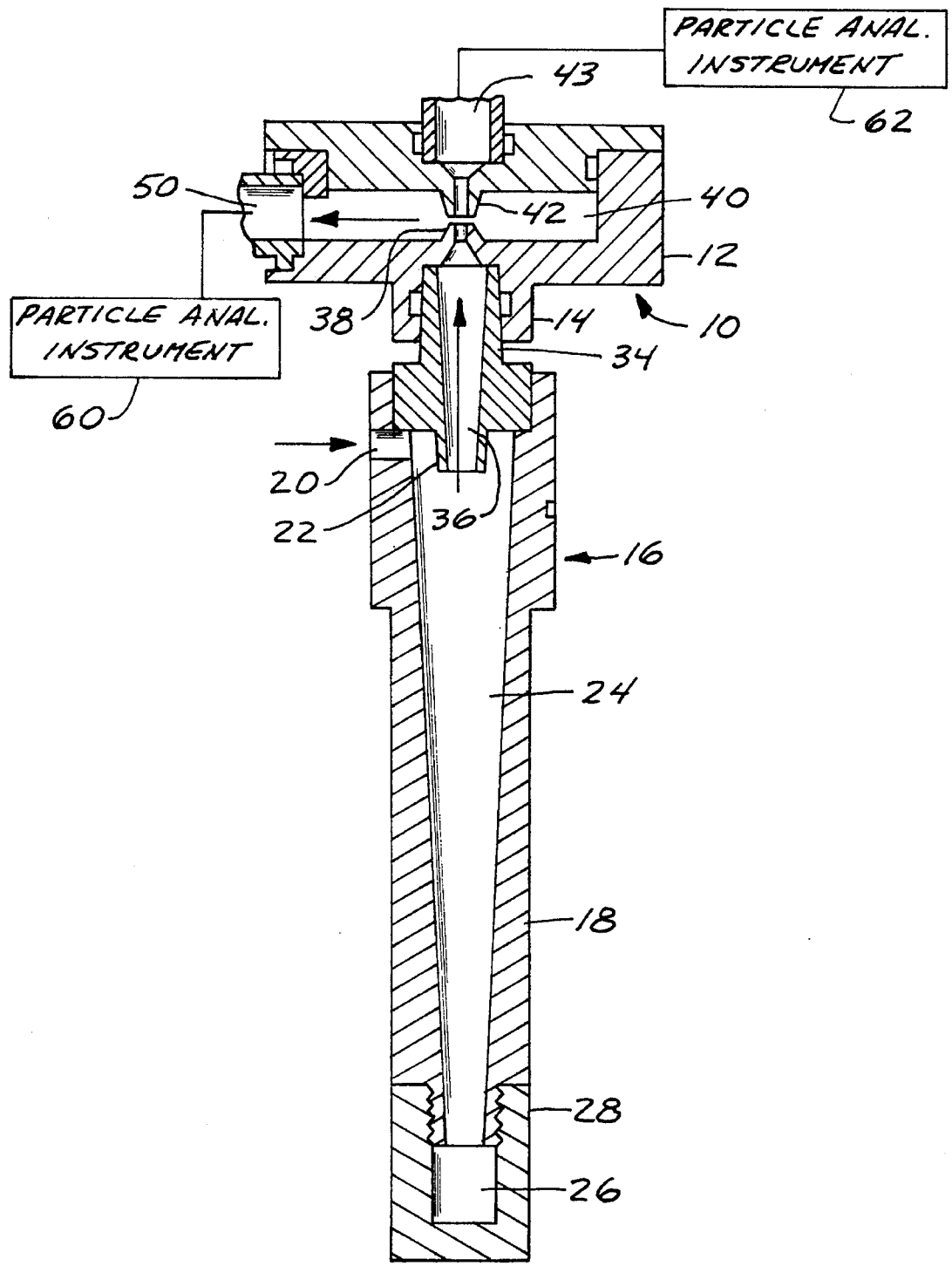

DIESEL PARTICLE VIRTUAL IMPACTOR SAMPLER

BACKGROUND OF THE INVENTION

The present invention relates to determining the presence of small particles, such as those from Diesel exhaust in an air sample.

Research has shown that coal mines utilizing diesel powered equipment produce a bimodal distribution of aerosol particles. Diesel exhaust particles are primarily smaller than about 0.8 microns, while coal dust particles are larger.

It is important to measure the concentration of diesel and coal particles in order to monitor the air quality of air that is being breathed. Various samplers have been advanced to collect the respirable size particles in a mine.

U.S. Pat. No. 4,941,899 illustrates a personal aerosol sampler that has a two stage operation with a standard cyclone separator providing removal of large nonrespirable particles before the air being sampled was introduced into a secondary cyclone sampler. The secondary sampler initially separates out particles below about 0.8 microns from larger particles, and has a cup for collecting the larger particles for analysis. It has been found that this type of a separator can become overloaded, or some large particles can be re-entrained and then will be collected with the smaller diesel particles so that erroneous results may be given.

SUMMARY OF THE INVENTION

The present invention provides an inertial classifier that separates out nonrespirable particles that are above the respirable size particles from an airflow, and then provides the airflow through a virtual impactor that has a major flow carrying particles smaller than about 0.8 microns, which is the commonly accepted cutoff size for diesel exhaust particles. The virtual impactor has a minor flow carrying the larger particles. Two separate filters are preferably used, one for collecting the particles smaller than about 0.8 microns and the other collecting the particles carried with the minor flow, which are larger than about 0.8 microns. The two filters are of a type that can remove large amounts of material from the airflow without becoming overloaded, and particle re-entrainment into the fluid sample stream is impossible.

The output of the preclassifying cyclone separator is directed to the input of the virtual impactor where remaining particles are separated and separately captured.

The virtual impactor reliably separates and collects respirable particles that are from diesel exhaust. The filter type and size can be varied to suit the desires of the user.

BRIEF DESCRIPTION OF THE DRAWINGS

FIG. 2 is a vertical sectional view showing a device similar to that of FIG. 1, made to be connected to instrumentation as opposed to utilizing filters.

DETAILED DESCRIPTION OF THE PREFERRED EMBODIMENTS

Figure 1:
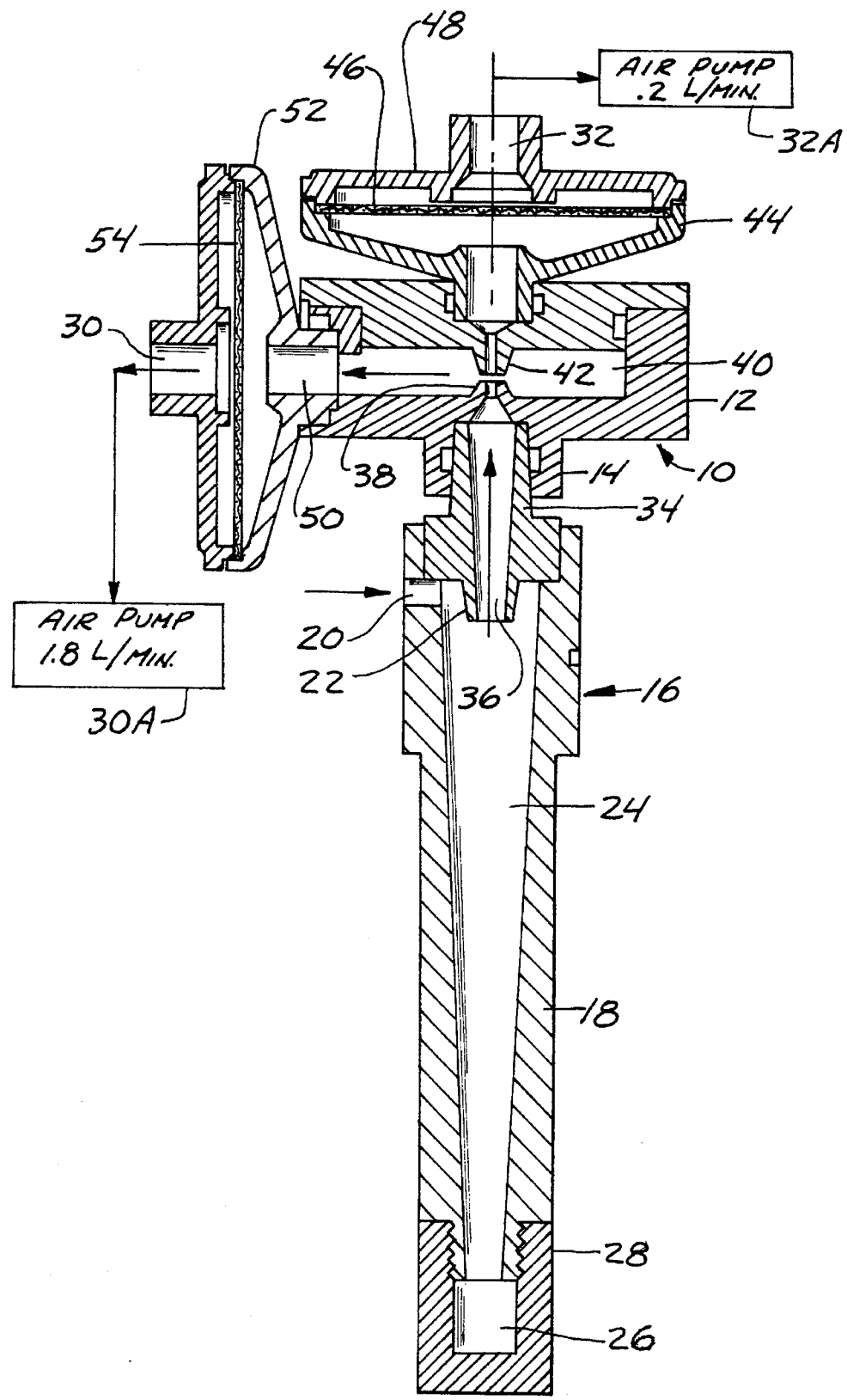
FIG. 1 is a sectional view through a virtual impactor sampler made according to the preferred embodiment of the present invention.

Referring to FIG. 1, a virtual impactor sampler made according to the present invention is indicated generally at 10, and includes a virtual impactor housing 12 that has an inlet hub 14. A cyclone type separator indicated at 16 is connected to the inlet 14. The cyclone separator has a cyclone body 18, with a flow inlet opening 20 that directs in flowing air around a tubular nozzle 22 so that particles will tend to swirl around the nozzle on the interior chamber 24 of the cyclone separator and the inertia of the larger particles will cause them to drop out and either stick to the walls of chamber 24 or fall into a trap 26. The trap 26 is formed in a cap 28 that can be unscrewed from the body 18 for removing the collected large particles.

The airflow at the inlet 20 of the cyclone is provided by a controlled outlet flow from the virtual impactor housing 12. The virtual impactor housing 12 has two outlets, including an outlet 30 for major flow and a minor flow outlet 32. These outlets 30 and 32 are connected to suitable air pumps illustrated schematically at 30A and 32A. The virtual impactor housing 12 and the inlet opening 14 support a nozzle member 34 that has an interior passageway 36 that expands in direction toward a virtual impactor nozzle 38 on an interior chamber 40 of the virtual impactor housing. The nozzle 38 aligns with a minor flow receiving tube 42. The minor flow passes through the receiving tube 42 and carries particles larger than the cutoff size into a filter housing 44. The filter housing supports a filter 46 of desired filtering capacity, which is removably held in place with a filter housing cover 48. The outlet passageway 32 is formed in the filter housing cover 48.

The major flow provided by pump 30A through the outlet 30 flows from the chamber 40. The flow passes from the space between nozzle 38 and receiving tube 42 laterally into chamber 40. The major flow moves laterally from the space between the nozzle 38 and receiving tube 42 carries smaller particles with the flow. The major flow moves through a passageway 50 leading to a major flow filter housing 52 that supports a second filter 54. A filter cover 56 clamps the filter 54 relative to the housing 52.

Nozzle 38 and receiving tube 42 and the spacing of the nozzles are designed utilizing known procedures so that there is about a 0.8 micron cutoff for the smaller particles that are carried with the major flow through the chamber 40 through filter 54 and out the outlet passageway 30. Particles smaller than about 0.8 microns are captured on the filter 54.

Particles larger than about 0.8 microns, and smaller than the nonrespirable particles separated out by cyclone separator 16, or other large particle classifier, for example, particles larger than a selected cutoff size of 10 microns will be carried by inertia from nozzle 38 out of the chamber directly to and through the receiving tube 42 and into the filter housing 44. The larger particles will be deposited on the filter 46 before the air of the minor flow is carried through the outlet 32.

The about 0.8 micron cutoff size virtual impactor insures that both the respirable coal dust, which is larger than about 0.8 microns and the respirable diesel particles, which are less than about 0.8 microns remain airborne until they are collected on the respective filters. The cyclone separator 16 or other classifier will remove nonrespirable particles. A major improvement is that a system is developed that is compatible with personal sampler equipment, and provides positive control for both the minor and major flows of the virtual impactor, without any opportunity for overloading a cyclone or obtaining erroneous results.

While the total flow design shown is 2 liters per minute, and the major flow is set at 1.8 liters per minute, with the minor flow being 0.2 liters per minute, the major and minor flow volumes can be changed. Instead of having the cyclone for a preclassifying device for removing large, nonrespirable particles, a different type classifier, with some other particle cutoff size could be utilized as well. If no substantial number of large particles are present, and that is known, the pre-classifier can be eliminated. The cutoff size can also be adjusted in the virtual impactor using known techniques if about 0.8 microns is not desired.

Additionally, virtual impactors with more than one set of nozzles and receiving tubes can be used. The description shows one such set, but several sets can be used with the classified particles captured on one or more filters. Thus, the use of multiple impactor nozzles is easily accomplished.

FIG. 2 illustrates the same sampler as in FIG. 1, but the outlets comprising a passageway 43 and passageway 50 from the virtual impactor housing 12 are directed to provide both minor flows and major flows to aerosol analyzing instruments indicated at 60 and 62, respectively. The filters will not be used.

The analyzer instrument can be a photometer, for counting the particles so that an idea of the concentration of the particles can be obtained in the air being breathed. The size of the unit can be quite easily controlled, and the air pumps can be battery powered if desired for permitting use as a personal sampler.

The unit using the filters can be made for personal use and carried by a person. The air pumps can be battery powered and run for selected periods of time. The size is kept small for use.

Although the present invention has been described with reference to preferred embodiments, workers skilled in the art will recognize that changes may be made in form and detail without departing from the spirit and scope of the invention.

What is claimed is:

1. A virtual impactor sampler of size to be carried on a person comprising a virtual compactor having an inlet passage having a first axis defining an axis of flow and a housing having a chamber into which the flow from the inlet passage passes, the inlet passage terminating in an inlet nozzle coaxial with the first axis, the inlet nozzle opening to the chamber in the housing;

an outlet nozzle providing an outlet from the chamber coaxial with the inlet nozzle and spaced from the inlet nozzle to form a virtual impactor section within the chamber of the housing;

a first pump for providing a major flow of air through the inlet nozzle and then laterally of the axis through a first outlet from the chamber;

a first filter for filtering the major flow of air from the first outlet, said first filter having a flat filter member defining a plane positioned parallel to the first axis, and positioned laterally of the housing;

a second filter having an inlet connected to the outlet nozzle and centered on the first axis;

a second pump establishing a minor flow of air through the outlet nozzle and the second filter, the second filter having a flat filter member with a plane perpendicular to the first axis, the first and second filters overlapping in direction along the first axis, the major and minor flows being set for determining particle concentration above and below a particle size cutout point selected to separate and collect diesel exhaust particles.

2. The virtual impactor sampler of claim 1, a particle classifier mounted with an axis coinciding with the first axis that removes nonrespirable particles substantially larger than the particle size cutoff point of the virtual impactor prior to introduction of flow through the inlet passage.

3. The virtual impactor sampler of claim 1, and a cyclone separator connected to the inlet passage for removing particles substantially above the cutoff point of the virtual impactor.

* * * * *